(12) United States Patent
Rottger et al.

(10) Patent No.: US 9,333,483 B2
(45) Date of Patent: May 10, 2016

(54) ABSORBENT STRUCTURE

(71) Applicant: Glatfelter Falkenhagen GmbH, Pritzwalk (DE)

(72) Inventors: Henning Rottger, Kaltenkirchen (DE); Reno Volkmer, Falkenhagen (DE)

(73) Assignee: GLATFELTER FALKENHAGEN GMBH, Pritzwalk (DE)

( * ) Notice: Subject to any disclaimer, the term of this patent is extended or adjusted under 35 U.S.C. 154(b) by 0 days.

(21) Appl. No.: 14/096,637

(22) Filed: Dec. 4, 2013

(65) Prior Publication Data

US 2014/0094361 A1  Apr. 3, 2014

Related U.S. Application Data

(60) Division of application No. 13/481,512, filed on May 25, 2012, now Pat. No. 8,603,622, which is a continuation of application No. PCT/EP2010/007186, filed on Nov. 26, 2010.

(30) Foreign Application Priority Data

Nov. 27, 2009  (DE) .......... 10 2009 055 951

(51) Int. Cl.
*B32B 37/14* (2006.01)
*A61F 13/15* (2006.01)
*A61F 13/537* (2006.01)
*B01J 20/26* (2006.01)
*A61F 13/534* (2006.01)
*A61F 13/53* (2006.01)

(52) U.S. Cl.
CPC .......... *B01J 20/26* (2013.01); *A61F 13/15658* (2013.01); *A61F 13/534* (2013.01); *A61F 13/53747* (2013.01); *A61F 13/53756* (2013.01); *A61F 2013/530532* (2013.01); *A61F 2013/530897* (2013.01); *Y10T 428/24612* (2015.01); *Y10T 428/24942* (2015.01); (Continued)

(58) Field of Classification Search
USPC ........ 162/109, 117, 141, 157.1, 157.2, 157.4, 162/158, 164.1, 168.1, 164.7; 428/98, 154, 428/156, 172, 212; 502/402; 604/358, 365, 604/367, 372, 378, 379, 385.01
See application file for complete search history.

(56) References Cited

U.S. PATENT DOCUMENTS 5,547,745 A  8/1996  Hansen et al.
6,420,626 B1  7/2002  Erspamer et al.
(Continued)

FOREIGN PATENT DOCUMENTS

DE  69727495 T2  6/1998
DE  69808061 T2  10/1998
(Continued)

OTHER PUBLICATIONS

Smook, Gary A., Handbook of Pulp and Paper Terminology, Angus Wilde Publications, 1990, p. 163.*

*Primary Examiner* — Dennis Cordray
(74) *Attorney, Agent, or Firm* — Blank Rome LLP

(57) ABSTRACT

An absorbent structure with a sequence of two layers includes at least one liquid absorption layer, a subsequent liquid storage layer with super absorbent polymer particles and super absorbent polymer fibers, and a subsequent liquid distribution layer. The layers are connected and form a sheet structure. The liquid storage layer has its super absorbent polymer extending from the liquid storage layer into the liquid distribution layer in order to generate a return suction effect for the liquid that has passed through the liquid absorption layer and liquid storage layer into the liquid distribution layer.

7 Claims, 6 Drawing Sheets

(52) U.S. Cl.
CPC   *Y10T428/24996* (2015.04); *Y10T 428/249953* (2015.04); *Y10T 428/249977* (2015.04); *Y10T 428/249981* (2015.04); *Y10T 428/249986* (2015.04)

(56) References Cited

U.S. PATENT DOCUMENTS

| | | | |
|---|---|---|---|
| 6,503,854 | B1 | 1/2003 | Abuto et al. |
| 2003/0139718 | A1 | 7/2003 | Graef et al. |
| 2003/0195485 | A1 | 10/2003 | Rangachari et al. |
| 2003/0234468 | A1 | 12/2003 | Rangachari et al. |
| 2005/0165371 | A1 | 7/2005 | Giacometti |
| 2006/0206071 | A1 | 9/2006 | Graef et al. |
| 2008/0082067 | A1 | 4/2008 | Weerawarna et al. |
| 2012/0302983 | A1* | 11/2012 | Rottger et al. ............... 604/374 |

FOREIGN PATENT DOCUMENTS

| | | |
|---|---|---|
| DE | 69821794 T2 | 5/1999 |
| DE | 19918343 A1 | 10/2000 |
| DE | 10218259 A1 | 11/2003 |
| DE | 10232078 A1 | 3/2004 |
| DE | 00948502 T1 | 5/2004 |
| DE | 10251137 A1 | 5/2004 |
| DE | 10327026 A1 | 1/2005 |
| DE | 10355919 A1 | 6/2005 |
| DE | 102004005417 A1 | 8/2005 |
| DE | 102004009556 A1 | 9/2005 |
| DE | 102004015686 A1 | 10/2005 |
| DE | 102004021453 A1 | 11/2005 |
| DE | 60026791 T2 | 3/2006 |
| DE | 60304013 T2 | 3/2006 |
| DE | 102004056154 A1 | 5/2006 |
| EP | 0159630 A2 | 10/1985 |
| EP | 0600454 A1 | 6/1994 |
| WO | 95/03019 A1 | 2/1995 |
| WO | 00/74620 A1 | 12/2000 |
| WO | 03/000163 A1 | 1/2003 |
| WO | 03/034963 A2 | 5/2003 |
| WO | 03/086259 A1 | 10/2003 |
| WO | 2005/041815 A2 | 5/2005 |
| WO | 2005/061120 A1 | 7/2005 |
| WO | 2005/080655 A1 | 9/2005 |

* cited by examiner

ABSORBENT STRUCTURE

BACKGROUND OF THE INVENTION

1. Technical Field

The present invention relates to an absorbent structure including a liquid absorbent layer, a liquid storage layer and a liquid distribution layer using cellulose fibers and preferably super absorbent polymer particles, abbreviated as SAP particles. The super absorbent polymer can also be provided in another form, for example, through a fiber structure. Preferably, the absorbent structure is mostly made from cellulose fibers.

2. Description of the Background Art

Air laid products using cellulose and super absorbent polymer particles have been known for years and are used as a layer material in hygiene products, medical products and industrial products.

For example, WO00/74620 describes a uniform absorbent structure using air laid material, cellulose fibers and binders, preferably based on latex and/or polyolefin containing bi-component fibers, wherein the structure includes a liquid absorbent layer, a liquid storage layer and a liquid distribution layer with a respective pore structure, wherein the mean pore size of each layer decreases with a gradient in a direction from the absorbent layer to the distribution layer.

In the products known so far, a capillary effect is used for transporting liquids in which the capillary effect is generated through a selection of the pore structure in order to move the liquid in a controlled manner into a storage position and to reduce undesirable back wetting effects which can occur through run out of liquid from a liquid absorbent layer into a liquid distribution layer and beyond, for example onto the skin of a carrier of a hygiene product.

Therefore, it is desirable to have a product available through which back wetting effects of this type can be prevented and simultaneously a very efficient use of the absorption power of super absorbent components is provided.

SUMMARY OF THE INVENTION

Therefore it is an object of the present invention to provide a product and a method and a device for producing the product which prevents back wetting while providing an optimal use of an absorption power of super absorbent components.

The object is achieved with an absorbent structure, a method for producing on absorbent structure and a device according to the independent claims. Preferred embodiments are defined in the dependent claims. One or plural features from these embodiments, however, are also linkable with other features from the subsequent description to form additional embodiments and are not limited to the respectively claimed embodiment. Also the respectively proposed features in particular also of the respective dependent claims are only a first approach, wherein one or plural of the features can be supplemented and/or replaced with the subsequent features.

An absorbent structure is proposed with a sequence of two layers including at least one liquid absorbent layer, a subsequent liquid storage layer with super absorbent polymer SAP, preferably configured in the form of SAP particles and/or SAP fibers and a subsequent liquid distribution layer, wherein the layers are connected and form a layer structure. Thus, at least the liquid storage layer and the liquid distribution layer at least respectively include an air laid material as main component, preferably an air laid layer, which includes cellulose fibers. At least the liquid storage layer includes SAP particles. The super absorbent polymer of the liquid storage layer, preferably provided in the form of SAP particles and/or SAP fibers, extends partially into the liquid distribution layer and thus comes into direct contact with the liquid which is distributed in the liquid distribution layer of the product. The super absorbent polymer causes a back suction effect for the liquid which has entered through the liquid absorption layer and the liquid storage layer into the liquid distribution layer.

According to another embodiment, it is provided that the liquid absorption layer includes an air laid material. Preferably this layer at least to a major portion is made from cellulose fiber. It can furthermore be provided that the liquid absorption layer includes thermoplastic fibers. These fibers can be for example gluing fibers. For example, bico fibers, in particular core-jacket-fibers can be used in which the jacket has a lower melting point than the core. Another configuration provides that the liquid absorbent layer includes a voluminous fleece made from thermoplastic fibers. The voluminous fleece according to one embodiment is a carded fleece. One embodiment provides that the voluminous fleece is a hot air solidified fleece made from thermoplastic fibers. According to one embodiment, staple fibers are being used. The voluminous fleece can include fibers made from polyester, polypropylene, viscose and/or polyethylene. The voluminous fleece according to one embodiment can have a weight per unit area of 30 to 90 g/m$^2$. An embodiment for a usable material is Paratherm Loft 142/25 made by TWB Corporation.

Preferably, all layers of the absorbent structure are produced in an in-line process. Furthermore, there is the option that at least one layer of the absorbent structure is at least prefabricated and supplied to the manufacturing process as an intermediary product. Thus, the intermediary product can be rolled onto a winder and subsequently rolled off again at the production line and supplied to the process. One embodiment provides that, for example, a layer is provided which is used as a liquid absorption layer in the subsequent absorbent structure. Another embodiment provides that, for example, a prefabricated layer is provided which functions as a liquid distribution layer in the subsequent finished absorbent structure. Another embodiment provides that at least one of the layers can also be configured with multiple layers. For example, the liquid distribution layer can be connected with another layer, preferably with a smaller pore size than the fiber layer provided with the liquid distribution layer, for example a tissue layer. A preferred embodiment provides that the tissue layer is arranged directly adjacent to the air laid layer and connected with the air laid layer which forms the liquid distribution layer. The tissue can support liquid distribution through having a smaller pore size than the air laid layer. The smaller pore size also causes a higher capillary force. The tissue for example can form an outside of the absorbent structure. A voluminous fleece made from thermoplastic fibers, preferably staple fibers can for example form the other outside of the absorbent structure.

Using a thermoplastic material in the liquid absorption layer facilitates for example an improvement of the recurring wetability. Thermoplastic fibers prevent absorption of liquid in the liquid absorption layer. Instead, the liquid is passed on to the liquid storage layer. Therein the liquid is stored, wherein a portion of the liquid can also get into the liquid distribution layer. From there, the liquid is distributed for example along the distribution layer before it is sucked back into the liquid storage layer.

In case the suction force of a super absorbent material (SAP) is significantly higher than a capillary force of respective layers of the product, it is feasible to transport liquid, which moves through the gradient of the capillary force from the liquid absorbent layer through the liquid storage layer into the liquid distribution layer and which is distributed therein, from the liquid distribution layer into the liquid storage layer and to store it there in the super absorbent materials.

One embodiment provides that the liquid storage layer includes open cavities and/or portions with large pores in its interior. The portions can be used so that the super absorbent material expands into them after the receiving the liquid when the super absorbent material swells. The cavities can used, for example, so that super absorbent material distributes in this direction, in particular during the production process of the absorbent structure. For example, this can be provided through vibrating during the production process.

According to one embodiment, the absorbent structure includes a gradient with respect to a pore structure which supports an outflow from the liquid absorbent layer towards the liquid distribution layer. The gradient structure can extend within one layer but can also extend over plural layers. The gradient can preferably cause an increase of the capillary force. A gradient is adjustable, for example, through the form of deposition of the cellulose fibers through additional compression and/or reduction of the pores through additional means, for example, supplying liquid or binder which reduces the size of the pores or partially plugs the pores. This can be on provided for example through latex wetting.

A pore size can be determined through image generating methods. Thus, for example, a cut is performed along a longitudinal surface of a layer structure. Therefore, the material is, for example, cooled down so that it can be cut without destroying the structures within the layer during cutting. The cut is then photographed and evaluated through image processing methods. A gradient is generated, for example, in that the pore size decreases transversally to a layer. Thus, the number of pores in the section is measured and their respective size is determined. Through forming a ratio of both sizes, namely the number of pores and the sum of their respective size, a mean pore size for this layer can be determined. A cross-section to be examined should be at least 20 mm×20 mm.

A preferred method for producing a section is using a cryoscopic fracture or cut with an extremely sharp blade, preferably through a microtome. A section surface thus produced can subsequently be evaluated, for example, through taking a picture of the cut surface and subsequently preferably automatic counting. There is also the option to generate a scanning electron microscope image which is subsequently evaluated. This is performed, for example, by the Saxonian Institute for Textile Research, STFI in Chemnitz, Germany in a standardized manner.

Besides forming a gradient along a layer, a gradient can also be provided in a layer transversally thereto. The gradient can, for example, be determined through a method as described supra.

A first gradient comparing the particular layers can, for example, also be accessed through an assessment of the respective cross-section perpendicular to the longitudinal extension of a layer. This gradient is therefore designated as total layer gradient. A second gradient comparing the particular layers can for example be determined in that the uppermost and the lowest transversal layer of a respective layer are considered. These are, for example, compared with one another. From this information can be derived whether a layer has a higher resistance against liquid exit in upward direction or in downward direction. Both layers can also be respectively determined with respect to their respective mean pore size. Thus, a respective threshold value of a mean pore size of the layer is determined. For example, a mean can be formed again from the two threshold values, wherein the mean is designated as threshold gradient. It is preferable when the respective threshold value gradient and the respective threshold value respectively increase viewed over a layer structure.

Another embodiment provides, for example, that the mean pore size in a transition from one layer to another layer respectively decreases from the liquid absorption layer to the liquid distribution layer.

The absorbent structure has the advantage that liquid which runs from the liquid absorption layer into the liquid storage layer during use of the absorbent structure is absorbed and preferably also distributed which prevents back wetting effects through liquid run out. A distribution of liquid, however, is not only performed into a longitudinal direction within the liquid distribution layer. It has rather become apparent that a back flow can be adjusted through a controlled adjustment, arrangement and distribution of the SAP particles and/or SAP fibers between the two layers, wherein the liquid is already absorbed through the SAP particles and/or the SAP fibers in the liquid distribution layer and then moves back through the SAP particles and/or SAP fibers into the liquid storage layer. This mechanism can be supported for example through an adjustment of the porosity of the air laid material used. According to one configuration, a material can be used herein as derived for example from WO 00/74620. A gradient of this type with respect to density and/or porosity can for example also be used herein. In the structure described in WO 00/74620 including the liquid absorption layer, liquid storage layer and liquid distribution layer besides the gravitation force only a capillary force is provided which is oriented from the liquid absorption layer to the liquid distribution layer. Thus, in the structures described in WO 00/74620, a backflow of the liquid from the liquid distribution layer into the liquid storage layer is physically not possible. The technical teachings thus proposed, however, lead to a facilitation of an embodiment of a backflow.

One embodiment provides that the SAP particles and/or SAP fibers protrude in an uneven manner into the liquid distribution layer from the liquid storage layer. Another embodiment provides that there are portions into which no SAP particle and/or SAP fiber protrudes into the liquid distribution layer from the liquid storage layer while in adjacent portions at least the majority of the SAP particles and/or SAP fibers, this means at least 50% protrude into the liquid distribution layer from the liquid storage layer. Another configuration provides that there are portions within which fewer SAP particles and/or SAP fibers protrude into the liquid distribution layer from the liquid storage layer compared to adjacent portions, in particular compared to portions in which at least the majority of the SAP particles and/or fibers protrude into the liquid distribution layer from the liquid storage layer.

It is preferred when the absorbent structure includes SAP particles and/or SAP fibers which at least by a third of a longitudinal extension protrude into the liquid storage layer. A protrusion of the longitudinal extension can, for example, depend on which thicknesses the various layers have. It is preferred when the SAP particles and/or SAP fibers protrude at least far enough into the liquid distribution layer so that they protrude by 10%, preferably 25% of a thickness of the liquid distribution layer into the liquid distribution layer.

In a SAP fiber, the length is determined in that its extension from beginning to end is measured as a shortest distance in the structure. This also applies for wound SAP fibers. SAP fibers can be used approximately straight and also in a wound structure.

One embodiment provides that in an absorbing structure more than 20%, preferably more than 40% of the SAP particles and/or SAP fibers arranged in the liquid storage layer protrude into the liquid distribution layer. Another embodiment provides that more than 40% but less than 70% of the SAP particles and/or SAP fibers arranged in the liquid storage layer protrude into the liquid distribution layer.

It is furthermore preferred for an absorbent structure that the SAP particles and/or SAP fibers protruding into the liquid distribution layer after liquid absorption have grown more in the liquid storage layer than in the liquid distribution layer. Thus, for example, the swelling capability of an SAP particle or an SAP fiber can be configured so that it extends in a direction of least resistance. When the liquid storage layer has less resistance, for example, through less density, a structure with more open pores, less bonding adhesion of the fibers amongst one another and/or through other means which can cause a resistance against distribution placement in a portion of the liquid storage layer and preferably the fibers, a swelling SAP particles or an SAP fiber can, for example, not only swell preferably in the liquid storage layer. Thus, for example, a movement of the swelling SAP particle or of the fiber can be performed back into the liquid storage layer. According to a preferred embodiment it is provided that SAP particles and/or SAP fibers protruding into the liquid storage layer after liquid absorption have at least partially pulled back into the liquid distribution layer.

The super absorbent material, for example, provided in the form of the SAP particles and/or SAP fibers described supra is swell-capable and typically transitions into a gel type condition. Thus, the fibers cannot only store water. Rather, the SAP particles in an arrangement as described supra in the layer structure are capable of generating a suction flow and thus can be used for example as drainage material for the liquid distribution layer.

Chemically speaking, SAP can be co-polymers which include, for example, acrylic acid and sodium acrylate, wherein the ratio of the two monomers relative to one another can vary. Additionally, for example, cross linkers are added during polymerization, wherein the cross linkers connect the formed long chain polymers at some locations with one another through chemical bridges. The properties of the polymer can be adjusted as a function of the degree of cross linking. One configuration provides, for example, that two different SAP materials, for example, two different SAP particles, two different SAP fibers and/or SAP particles and SAP fibers that differ from one another and have properties that differ from one another are being used. Thus, the difference can be in the liquid absorption capability, the speed of liquid absorption, the swelling itself during liquid absorption, a time delay until the liquid absorption starts, a liquid absorption rate or another parameter. Various SAP materials can be arranged in a mixed manner and also separate from one another in various portions. The different portions cannot only be arranged in machine-direction and cross-direction of a processing with respect to an air laid production device. Rather also an arrangement along a thickness of the material can differ, thus, in particular, different portions can be configured.

For example, SAP materials can be used as they can be derived from EP 0810 886, in particular also from the prior art recited therein which is incorporated in its entirety by this reference. One embodiment provides, for example, that SAP particles include a coating. The coating, for example, can only dissolve in the presence of a liquid in order to facilitate reception of the liquid by the SAP particle in the first place. This is an option how, for example, a time delay of absorption and preferably sucking back liquid in the liquid distribution into the liquid storage system can be adjusted. For example, a first SAP material can be arranged in the liquid storage layer, wherein the first SAP material is not coated, and a second SAP material can be arranged which is coated. Through the liquid contact initially the first SAP material binds the liquid. Overflowing liquid enters the liquid distribution layer, wherein the second SAP material is only activated with a time delay after the liquid flows by or contacts the same. Thus, the second SAP material is configured in particular to act as drainage and to suck back liquid in order to be able to establish a back flow into the liquid storage layer. Thus, it can be provided that the second SAP material essentially protrudes into the liquid storage layer, the first material, however, hardly protrudes in the liquid storage layer or does not protrude in the liquid storage layer at all. This is adjusted, for example, through the layer structure and also through the subsequent pressure onto the generated layer structure.

Furthermore SAP material can be used as can be derived respectively from DE 10 2004 015 686 A1, DE 698 217 94, and/or DE 10 2004 005 417 A1 respectively, in particular with reference to the configuration and the structure, the geometry of the super absorbent polymer and also the materials and manufacturing methods used. Reference is made to these printed documents in an exemplary manner in the context of the disclosure. Another embodiment provides that the SAP particles are provided granulate shaped and that they can also have another geometry; for example they can be provided in the form of fibers or in other forms. Fibers comprising a certain amount of super absorber can be derived from DE 10 232 078 A1 and also DE 10 251 137 A1. Also these documents are incorporated in their entirety by this reference.

Another embodiment provides that the properties of the SAP are adjusted in a controlled manner, preferably as a function of the liquid to be absorbed, but also as a function of the absorbing product and the respectively prevailing conditions for the SAP. There is the approach AAP which stands for absorption against pressure in order to demonstrate how SAP can absorb in spite of pressure. Thus, there is the WSP-EDANA-Method WSP 242.2 (05). Furthermore, the SAP can be described through the so called free swell capacity according to the method WSP 240.2 (05). There is also the possibility to consider the centrifuge retention capacity (CRC) WSP 241.2 (05). A preferred embodiment provides to describe a characterization of the SAP's based on the ratio of "absorption against pressure" to "free swell capacity". According to one configuration, an SAP is used with a CRC-value of 30-35 g/g and an AAP value depending on the cross link value of 18-24 g/g.

Preferably the swelling pressure of the SAP for sucking up liquid from the liquid distribution layer into the liquid storage layer is used. Thus, the SAP includes, for example, a swelling pressure in the amount of 6-8 bar, accordingly approximately 80-90 meters water column. This value is much higher compared to a capillary force which can develop for SAP with a water column of less than 1 meter. The swelling pressure can thus be used as a vertical force in order to retrieve the liquid from the liquid distribution layer into the liquid storage layer.

In one embodiment, the absorbent structure is configured as a layer structure, wherein the layer structure includes at least one boundary area and wherein the layer structure includes cavities within the liquid distribution layer and/or the liquid storage layer and/or the liquid absorption layer and/or a boundary area between the liquid distribution layer and the liquid storage layer and/or the liquid absorption layer.

These cavities can be generated, for example, when producing the absorbent structure. For example, in that the layers are connected which forms the layer structure and wherein during the binding process a stretching of the layer structure is performed that is at least oriented in machine direction. The air laid layers are connected and compressed through thermal bonding, using binders and using calendering. Through this bonding process, the layer structure thus obtained can relax again, wherein the cavities within the air laid layers or at its boundary surfaces also relax and are visible in the absorbent structure as preferably irregular cavities in which preferably no cellulose fibers and preferably also no SAP particles and/or SAP particles are arranged.

Preferably, these cavities are configured larger in the liquid storage layer than in the liquid absorption layer and/or in the liquid distribution layer.

Another embodiment provides that the absorbent structure is configured so that at least a portion of the cellulose fibers of the air laid layers of the liquid distribution layer and/or of the liquid storage layer and/or of the liquid absorption layer are mixed with one another in the liquid boundary area.

Preferably, the air laid layers of the liquid distribution layer and/or of the liquid absorption layer transition into one another within the boundary area.

One embodiment provides that the air laid layers of the liquid distribution layer and/or the liquid storage layer and/or the liquid absorption layer within the layer structure are not differentiable from one another. Preferably, identical or similar cellulose fibers are being used. For example, the fibers are deposited at separate stations. After storage, however, two layers are not differentiatable from one another anymore based on a sharp phase boundary. Rather, the layers transition into one another or not more than two different layers are identifiable in a cross sectional view.

The absorbent structure can be configured so that the liquid distribution layer has a first and second surface, wherein the first surface is in contact with the liquid storage layer and wherein the liquid distribution layer is compressed to a greater extent at its second surface than at its first surface.

It has proven advantageous that the liquid storage layer has a higher density than the liquid distribution layer and/or the liquid absorption layer. A density computation is thus performed for the entire density of the layer; this means all components of a layer are included. Thus, the layer is measured and density is computed with reference to the dimension of the layer. Thus, as a result a mean density can be determined which characterizes the layer.

One embodiment provides that the SAP particles and/or the SAP fibers protrude from the liquid storage layer into the liquid distribution layer. It has become apparent that through the capillary force acting within the layer structure and within the particular air laid layers liquid flows initially from the liquid absorption layer to the liquid distribution layer. Through the SAP particles and/or SAP fibers protruding from the liquid storage layer into the liquid distribution layer a suction effect is generated which lets liquid flow from the liquid distribution layer back into the liquid storage layer. According to an embodiment it is provided that for a first liquid dispensing onto the liquid absorption layer the suction effect which is caused by the SAP particles and/or the SAP fibers is provided with a time delay relative to the suction effect through capillary effects. According to another embodiment, it is provided that for multiple liquid applications there is a superposition of transport processes for the liquid, wherein preferably the transportation through the capillary forces is typically performed quicker than the back transportation of liquid from the liquid distribution layer into the liquid storage layer through the super absorbent materials.

It has also proven advantageous to configure an absorbent structure so that at least one liquid absorption layer is provided and a liquid storage layer configured as a layer with plural layers, preferably a layer with two layers. For example, the liquid storage layer can be formed from at least:
 one layer, including an air laid layer, preferably including cellulose fibers and SAP particles and/or SAP fibers and at least one additional layer including SAP particles or
 two layers respectively including an air laid layer, preferably including cellulose fibers and SAP particles and/or SAP fibers.

Introducing super absorbent polymers preferably in the form of SAP particles and/or SAP fibers in another layer of the absorbent structure facilitates for example that the absorbent structure can take over the function of a liquid storage layer and also of a liquid distribution layer. The layer according to one embodiment preferably includes the highest density within the liquid storage layer or the liquid distribution layer of the layer structure and thus has very good liquid distribution properties. Furthermore, the layer can help to improve expansion properties of the layer structure for example also with respect to an elastic property. Another advantage is that the SAP particles and/or SAP fibers within the layer can expand very well and sufficient space is available for swelling which improves the absorption capabilities of the layer structure. Thus, an additional layer facilitates embedding a higher portion of SAP particles and/or SAP fibers. Thus, a product of this type can in particular fulfill the requirements of incontinence products.

Thus, the respective layers can include identical or different types of cellulose fibers and/or SAP particles and/or SAP fibers. This way the receiving properties of the particular layers of the layer structure can be adjusted in a defined manner.

For example, in one layer, highly permeable SAP particles and/or SAP fibers can be used which together with SAP particles and/or SAP fibers in another layer cause a two stage absorption and storage effect. For example, in one layer which is oriented towards the liquid absorption layer, SAP particles and/or SAP fibers with high absorption capability can be provided and in another layer semi permeable SAP particle and/or SAP fibers can be provided. Thus, a buffer function in another layer can be generated which is advantageous in particular when a liquid is applied several times.

In another embodiment the liquid absorption layer includes at least cellulose fibers and bi component fibers, wherein the liquid storage layer includes at least cellulose fibers and SAP particles and/or SAP fibers.

One embodiment provides that the bi component fibers have a core jacket structure. It is also provided that the bi component fibers include at least one PET. Advantageously, the bi component fibers includes at least one polyethylene preferably a LDPE or a LLDPE. In a bi component fiber with a core jacket structure, a polymer is provided in the core that includes PET or a poly propylene and a jacket is provided that includes polyethylene. The bi component fibers are preferably used as bonding fibers. Through heating the fibers are at least softened enough, so that they form a gluey surface at which cellulose fibers and other components of the layer but also components of adjacent layers are firmly attached during cooling. According to one embodiment cellulose bonding fibers can be used as they are derived from DE69808061 which is incorporated in its entirely by this reference.

Another embodiment provides that at least cellulose fibers and bi component fibers are provided in the liquid absorption layer. The liquid absorption layer includes at least cellulose fibers and SAP particles and/or SAP fibers. The liquid distribution layer in this embodiment mostly includes cellulose fibers and a bonding agent layer is provided preferably a latex layer.

The particular layers of the absorbing structure can include:
- respectively the same type of cellulose fibers,
- respectively different types of cellulose fibers,
- mixtures thereof,
- chemically and/or physically treated cellulose fibers,
- untreated cellulose fibers,
- mixtures of treated and untreated cellulose fibers,
- synthetic fibers by themselves, or mixed with cellulose fibers in treated or untreated form, and
- fibers with mineral origin by themselves or mixed with synthetic and/or cellulose fibers.

Particular fibers can also include cellulose fibers exclusively. A particular layer can thus be configured as liquid distribution layer or liquid storage layer or liquid absorption layer within the layer structure of the absorbent structure. A particular layer can also be configured as a layer in a multi layer liquid distribution layer or liquid storage layer or liquid absorption layer.

The term "cellulose fibers" in the context of the disclosure is not given a limited interpretation. Any types of natural fibers are useable which are capable or rendered capable through a chemical or physical treatment to absorb liquids and to preferably also bond liquids. Through a treatment of this type also synthetic fibers and fibers with mineral origin can be processed.

Chemical treatments can be for example the following:
- washing processes,
- extraction processes,
- bleaching processes,
- dying processes,
- fibrillation processes using solvents,
- surface treatment preferably for hydrophilization, increase of strength or elasticity for example through spraying, dipping, washing and similar.

A physical treatment can be performed through:
- particulation and fibrillation, for example, cutting, milling, breaking down into fibers,
- classing, for example, wind sifting.

It has proven useful that the liquid absorption layer includes an air laid layer which essentially includes chemically or physically non treated cellulose fibers. According to another embodiment, the cellulose fibers of the liquid storage layer are not treated chemically and/or physically. Another embodiment provides that the liquid absorption layer is configured as a cellulose free absorption layer or as an absorption layer that only includes a small amount of cellulose fiber and is configured as an air laid layer which, for example, includes thermoplastic fibers, such as staple fibers and the liquid distribution layer includes an air laid layer, which essentially includes chemically and/or physically treated cellulose fibers. By using thermoplastic fibers as major fiber component of absorption layer, a rewetting with liquids and further conduction into the liquid storage layer can be improved. Thus, in adaptation to an application, the fibers of the liquid absorption layer can be configured accordingly, for example, in a hydrophobic manner.

Particularly preferred cellulose fibers such as southern pine pulp types by Koch Cellulose LLC are produced through a pulping process and a bleaching process and have been finished. The fibers have an average fiber length of 2.7 mm, a density of $0.9 \text{ g/cm}^3$, a tensile strength of 414 kPa, a humidity of 8%, a defibulatable portion of over 99.5%, a specific absorption capability of 1.5 s/g.

These fibers due to their treatment are particularly suited for use in outer layers of the absorbent structure, such as the liquid storage layer and the liquid distribution layer. Depending on the type of fibrillation process for the fibers and the bleaching process, defined property combinations are achievable in the cellulose fibers.

It is provided that the chemical and/or physical treatment of the cellulose fibers of the air laid layer of the liquid absorption layer differs from the chemical and/or physical treatment of the cellulose fibers of the air laid layer of the liquid distribution layer.

In the liquid storage layer, preferably non treated fibers such as southern pine are used. This has various reasons. The pulp loses absorption capability through adding treatment agents in particular surface treatment agents. In order to provide best possible absorption in a liquid storage layer preferably a non treated pulp type is used. This pulp type can be best compressed in a process since the non treated fibers have good adhesion.

In the outer layers of the absorbent structure which are preferably formed by a liquid absorption layer and a liquid distribution layer, a treated cellulose pulp type is used due to the process in order to prevent adhesion at the devices used in a bonding process, for example an embossing roller in the calender arrangement. The surface treatment of the fibers furthermore reduces the adhesion between the fibers and thus improves compressibility of the fibers.

Cellulose fibers of Koch Cellulose LLC of the type GP 4821 are suitable for application in an outer layer of an absorbent structure since their voluminous structure is adapted to the requirements of a calendering process for compressing a layer structure.

According to one embodiment an absorbent structure is proposed, wherein:
- the liquid absorption layer includes at least cellulose fibers in a range between 60% by weight to 70% by weight and bi component fibers in a range between 30% by weight to 40% by weight with reference to the total weight of the liquid absorption layer,
- the liquid storage layer includes at least cellulose fibers and SAP particles and/or SAP fibers in a range between 15% by weight to 35% by weight with reference to the total weight of the absorbent structure and wherein
- the liquid distribution layer includes mostly cellulose fibers, preferably 100% by weight with reference to their total weight.

Furthermore, the absorbent layer can include another binder layer, such as a latex layer which is arranged on the liquid distribution layer.

A possible method for producing an absorbent structure can include the following steps, wherein the sequence of the steps is variable:
- depositing a first layer, preferably an air laid which preferably includes at least cellulose fibers and bi component fibers, and/or a highly voluminous fleece layer from thermoplastic fibers for configuring a liquid absorption layer which includes at least cellulose,
- depositing a second air laid layer for configuring a liquid storage layer which includes at least cellulose fibers and SAP-particles and/or SAP fibers,
- storing a third air laid layer for forming a liquid distribution layer,
- preferably applying the bonding agent layer,
- preferably applying a bonding agent layer, preferably a latex layer on one layer, preferably onto the layer structure thus obtained,
- preferably running the layer structure through heating devices in order to bond the layer structure, supplying at least one layer, preferably of the layer structure to a calender including at least one smooth roller and an opposite roller, preferably with protrusions which form a calender gap, compressing the at least one layer, preferably of the layer structure of the calendar, wherein SAP particle and/or SAP fibers protrude from the liquid storage layer into the liquid distribution layer and form a liquid removing contact between the liquid storage layer and the liquid distribution layer.

In particular, an absorbent structure is produced with a device of this type as described supra and as will be described in more detail infra.

One embodiment provides initially that a liquid distribution layer such as a pulp based distribution layer is placed by a first forming layer on a perforated band or pulled off from the perforated band. In a supplemental manner, in advance or subsequently, a tissue layer can be associated. Building on the liquid distribution layer, a storage layer and eventually an absorption layer is arranged. Based on this concept, a calender is provided which includes a roller with the embossing protrusions placed on the bottom so that the protrusions come in direct contact with the distribution layer or the tissue. A super absorbent material from the storage layer can only be vibrated into the lower distribution layer through the process with gravity support. This layer can be fixated through a subsequent heat and/or pressure treatment or another compression.

Another embodiment provides a method for producing an absorbent structure including at least the following steps:
depositing a first air laid layer for configuring a liquid storage layer which preferably includes at least cellulose fibers and bi component fibers,
depositing a second air laid layer for configuring a liquid storage layer which includes at least cellulose fibers and SAP materials, preferably SAP particles and/or SAP fibers.
depositing a third air laid layer for configuring a liquid distribution layer,
preferably applying a bonding agent layer, preferably a latex layer onto the layer structure thus obtained,
preferably running the layer structure through a heating device in order to bond the layer structure,
supplying the layer structure to a calender including at least one first smoothing roller and an opposite roller preferably with protrusions which form a calendering gap, and
compressing the layer structure in the calender gap, wherein SAP particles and SAP fibers protrude from the liquid storage layer into the liquid distribution layer and form a liquid removing contact between the liquid storage layer and the liquid distribution layer.

It is preferably provided that a SAP feed is provided between two subsequent forming heads for producing a respective air laid layer. This way the protrusion of the SAP material into the adjacent layer can be controlled in a particular manner. Thus, the liquid storage layer is formed by a forming head and the liquid distribution layer is formed by the other forming head. This way there is also the option that another SAP material is used when producing the liquid storage layer which is different from the SAP material which issued between the two other layers. However, there is also the option that other SAP materials are identical.

The cuts can be performed in the recited sequence or in another sequence.

One embodiment provides that a roller assembly is used for the method that has a set pressure through which a movement and a penetration of the SAP particles and/or SAP fibers deposited through the second air laid formation device is provided into the adjacent cellulose fiber portions. In particular the SAP particles and/or SAP fibers can be pressed into an adjacent portion of another layer.

According to one embodiment the calender can include two smooth rollers. The calender can include also one smooth roller and one roller with embossing protrusions. Furthermore, there is the option that additional heat is applied through a smooth roller which facilitates smoothing the surface of the layer structure. In this way, an open porosity of the surface of the material can be changed, in particular, it can be reduced. Another option for bonding can be derived from DE 102 18 259 A1 which is incorporated in its entirety by this reference.

A connection of air laid layers among one another and also of fibers in a particular air laid layer can be provided through melting the bonding agent layer and/or the SAP particles and/or SAP fibers. Other bonding agents, such as latex that is sprayed on, are also useable. Gluing agents can also be used which are sprayed on through a nozzle system. A bonding agent application can be performed over the entire surface or not over the entire surface, for example in the form of a regular or irregular pattern. A film can also be used which melts when the layers heat up so that it connects layers and/or fibers with one another.

One embodiment provides that the method includes an additional third air laid layer on the second air laid layer for forming a liquid absorption layer wherein the third air laid layer includes at least cellulose fibers and bi component fibers. It is also provided that the following steps are performed in the desired sequence in the process:
applying a latex layer onto the liquid distribution layer,
running the layer structure thus obtained through a heating device in order to activate the bi component fibers and to bond the cellulose fibers,
feeding the layer structure to a calendar, and
compressing the layer structure in the calender gap.

It has proven advantageous that the absorbent structure is produced in line. This can remove the boundaries between the particular layers of the absorbent structure and can provide a mixing of the fibers of respective layers adjacent to one another.

Besides that also producing the absorbent structure by using separate manufacturing steps is feasible, for example:
particular layers can be produced separately and bonded in a subsequent bonding process to form a layer structure which forms the absorbent structure,
prepregs or prelaminates and similar made from one or plural layers can be provided which are subsequently configured with other layers to form an absorbent structure.

Thus, the prepregs or prelaminates can include elements of one or plural functional layers. A functional layer can be a liquid distribution layer or a liquid storage layer or a liquid absorption layer or elements thereof such as a partial layer or a bonding agent layer or a layer with SAP particles and/or SAP fibers or a layer including bi component fibers.

According to another embodiment of the invention, a device for producing an absorbent structure is proposed which includes at least the following components:
a perforated band for depositing air laid layers for forming a layer structure,
a first air laid forming device from which at least cellulose fibers are pullable that form an air laid layer, a second air laid forming device from which at least cellulose fibers and SAP particles and/or SAP fibers are depositable on the air laid layer and preferably form a second air laid layer, a depositing device for another layer, an application device through which bonding agent, preferably a latex layer is applicable, a heating device in which bi component fibers and/or the bonding agent are activatable, a roller arrangement preferably a calender through which the layer structure is compressible, and a feed device for SAP particles and/or SAP fibers which are supplied at least in a dosed manner and preferably also in a position controlled manner and with partial penetration into the cellulose fibers of an air laid layer, wherein the cellulose fibers are adjacent to cellulose fibers of the second air laid forming device.

The sequence of the components can deviate from the sequence recited supra. In particular, an absorbent structure is produced with a device of this type as described supra and as will be described in more detail infra.

Furthermore preferably a device for providing bi component fibers is provided wherein the bi component fibers can be deposited together with the cellulose fibers on the perforated band and form an air laid layer. Also, a third air laid forming device through which at least cellulose fibers can be deposited on the perforated band can be integrated into the production equipment. For example, the absorbent structure can include three air laid layers which are connected with one another.

One embodiment includes an improvement of the device for producing an absorbent structure including at least the following:

a perforated band for depositing air laid layers for forming a layer structure, a first air laid layer forming device from which at least cellulose fibers are pullable and preferably a device for providing bi component fibers which are depositable together with the cellulose fibers on the perforated band and which form a first air laid layer, a second air laid forming device through which at least cellulose fibers and SAP particles and/or SAP fibers are depositable on the first air laid layer and preferably form a second air laid layer, wherein the second air laid forming device adds SAP particles in a dosed and a position controlled manner, a third air laid forming device through which at least cell fibers are depositable on the perforated band, an application device through which a bonding agent, preferably a latex layer is applicable to the layer structure, a heating device in which bi component fibers and/or bonding agents are activate able, a roller arrangement preferably a calender through which the layer structure is compressible and which has adjustable pressure through which a movement and penetration of the SAP particles deposited by the second air laid forming device into adjacent cellulose fiber portions is facilitated.

Another embodiment provides that between two forming heads, preferably between a second and a third forming head for producing a respective air laid layer a supply is provided through which at least one super absorbent material, preferably SAP particles and/or SAP fibers can be fed. A supply of this type can also be provided at another location along the device, additionally or alternatively.

A dosing of the SAP particles and/or SAP fibers can differ over the material width. There is also an option to arrange different SAP materials over the width of the material at different locations and also at identical locations in particular deposit the SAP. One embodiment provides that SAP particles are arranged in a different manner over a thickness of the material. A position control is provided for example through a controlled alignment of the SAP feed. There is also an option to perform this position control in an automated manner through sensors, image processing methods or similar. There is also an option that the SAP particles and/or SAP fibers are automatically checked in the layer for example through detecting the SAP particles and/or SAP fibers. Thus, SAP particles and/or SAP fibers can include a detectable identifier such as a special material, a color or another identifier. This facilitates a correction during the ongoing manufacturing process.

One embodiment provides a device, wherein in a calender besides a first smooth roller and an opposite roller with protrusions which form a first calender gap a second smooth roller is provided which is arranged relative to the opposite roller so that a second roller gap is formed in that during pass through of an absorbent structure with a liquid absorption layer the second smooth roller comes in contact with the liquid absorption layer. The smooth and embossing rollers are heatable, thus the liquid absorption layer receives additional compression and smoothing. In this arrangement, the liquid distribution layer of the absorbent structure comes in contact with the protrusions of the opposite roller.

The further processing of the absorbent structures can be performed subsequent to the layer production. The absorbent structures can also be rolled up while still adhering to one another or can be rendered transportable through a festooning unit. Further processing can then be performed at another location. Further processing can be a coating, additional laminating with one or plural other layers, cutting in longitudinal and transversal direction, another compressing and/or bonding, stretching and/or another step.

Components of an air laid production device and their relative application can be derived from DE 10 2004 009 556 A1 regarding production of a fiber web made from cellulose fibers, from DE 10 2004 214 53 A1 regarding a forming head and also regarding a method for producing an air laid layer, from DE 10 2004 056 154 A1 regarding a transport device. Furthermore, DE 10 327 026 A1 relates to a method for producing a fiber fleece using an air laid method and a fiber configured for the method. From DE 199 183 43 A1, an air laid method and an air laid layer can be derived in which a bonding fiber is also used. From WO 2005/080655 A1, the configuration of an air laid layer with different additional components and their layer arrangement and purpose can be derived. A detection of SAP and its controlled dispensing and possible correction and the production of absorbent structures separated from one another can be derived from WO03/034963 A2.

The documents recited supra and also the documents recited as prior are therein provide additional options how the device can be configured. For the disclosure of the invention these documents and also the prior art recited therein are incorporated in their entirety by this reference.

The absorbent structure can be used in:
  hygiene products such as baby diapers, female hygiene products, incontinence products, make up wipes,
  medical products such as operating room covers,
  industrial products such as cover mats, wipes, and
  food dishes for absorbing liquid.

Thus, the absorbent structure itself can form at least one exterior surface, preferably both exterior surfaces of a product. The absorbent structure can be at least covered, preferably connected with an additional layer at least on one side or at all sides.

Additional advantageous features and embodiments of the present invention are now described with reference to the subsequent embodiments which are also illustrated in more detail in the drawing figures. The features thus described are not limited to particular embodiments and can be combined into additional embodiments with the other features described supra, wherein these embodiments are not described in detail.

DETAILED DESCRIPTION OF THE INVENTION

Figure 1:
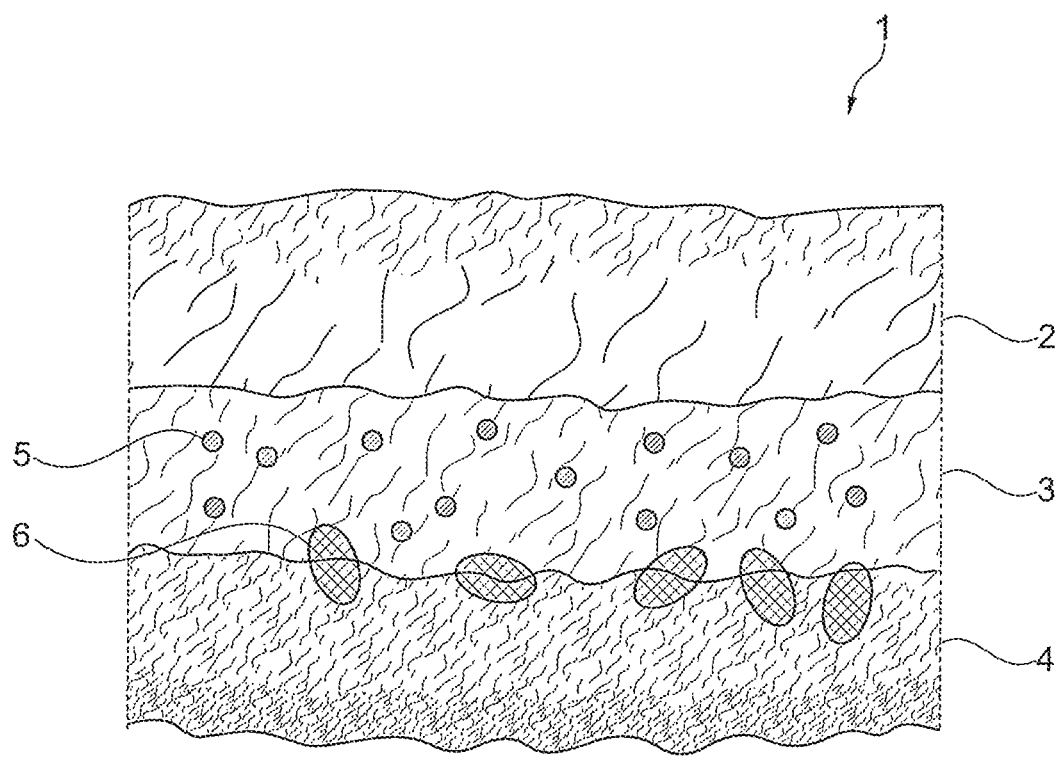
FIG. 1-FIG. 4 illustrate schematic cross sectional views of various bonded absorbent structures using air laid fleeces.

Turning to FIG. 1, therein illustrated is an absorbent structure generally designated by the reference numeral 1 and made from three layers of an air laid material which are arranged above one another and which have been connected with one another in a subsequent calendering process using heat and pressure. The layer structure includes the following layers:
 a liquid absorption layer 2 including cellulose and bi component fibers,
 a liquid storage layer 3 including cellulose fibers and first SAP particles 5 and second SAP particles 6; and
 a liquid distribution layer 4 including cellulose fibers.

Through the type of deposition process for the air laid layers and the type of bonding process which is used for producing the absorbent structure and which also in this case is an in line process, the particular air laid layers of the liquid distribution layer 4, the liquid storage layer 3, and the liquid absorbent layer 2 within the boundary portion have not transitioned into one another, wherein the fibers of adjacent portions are separated from one another through an identifiable boundary path. This boundary path for example can be clearly emphasized through different color differentiation of the fibers of different layers. The air laid layers are easily differentiated from one another within the layer structure. In both outer boundary layers, for example, a stronger compression of the fibers is evident. The first and the second SAP particles 5, 6 are arranged in the absorbent structure in a random distribution and are glued together with the fibers at least in a point form manner. In the center portion of the absorbent structure few small cavities are visible in which neither fibers nor SAP particles are arranged.

Figure 2:
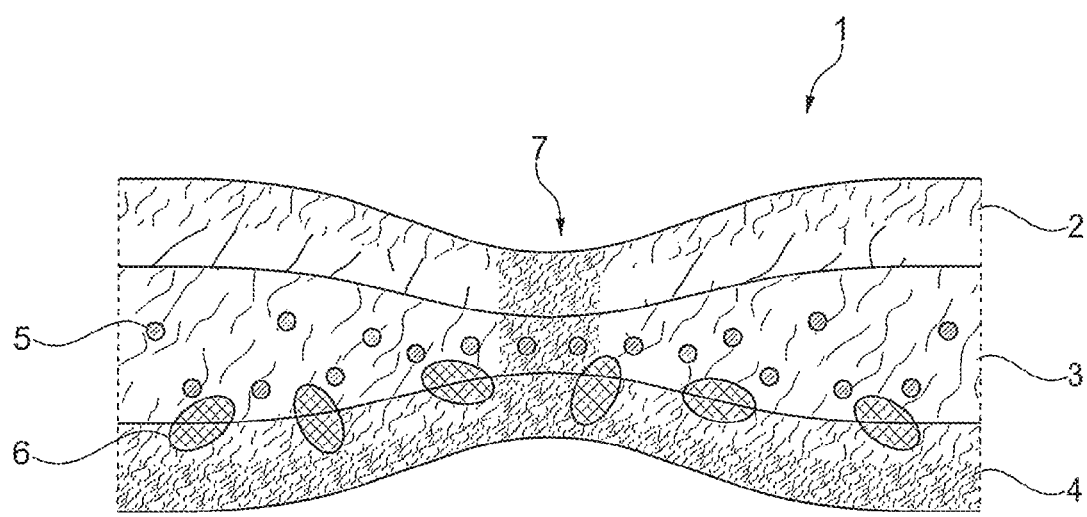

FIG. 2 illustrates a layer structure which depicts another location of the same material according to FIG. 1 in an exemplary schematic view. A bonding point 7 is clearly visible in which a much stronger compression of the material is provided. The air laid layers are further differentiable from one another in the layer structure in both figures. It is visible in FIG. 2 that preferably also at the two outer boundary layers of the absorbent structure 1 experience a stronger compression of the fibers than the center portion.

Figure 3:
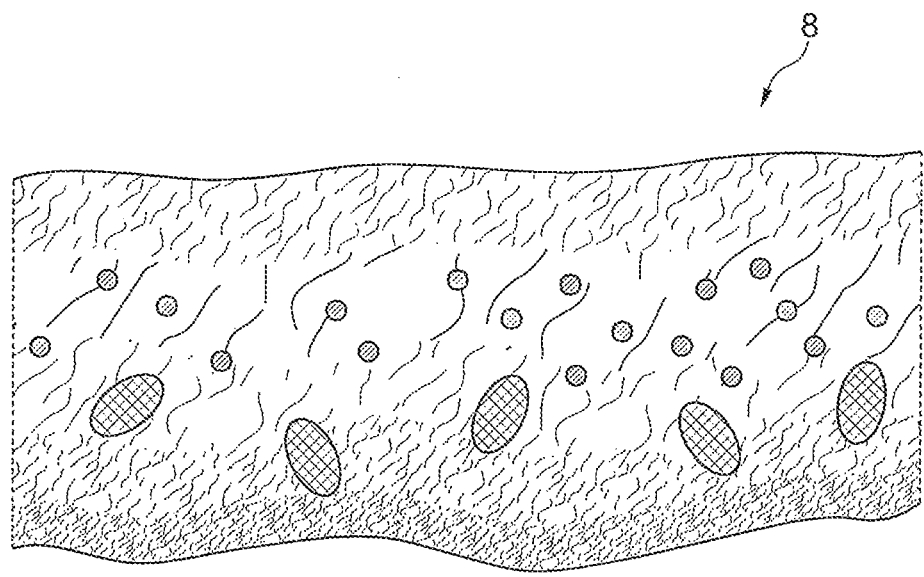

FIG. 3 illustrates a second layer structure 8 without the difference recited supra between the boundary portions and their respective center portion of the absorbent structure. Singular stronger compressions but also singular cavities are only slightly visible in the center portions and also in the boundary portions of the absorbent structure. The layers, however, transition into one another and do not have a clear boundary but a mixed portion.

Figure 4:
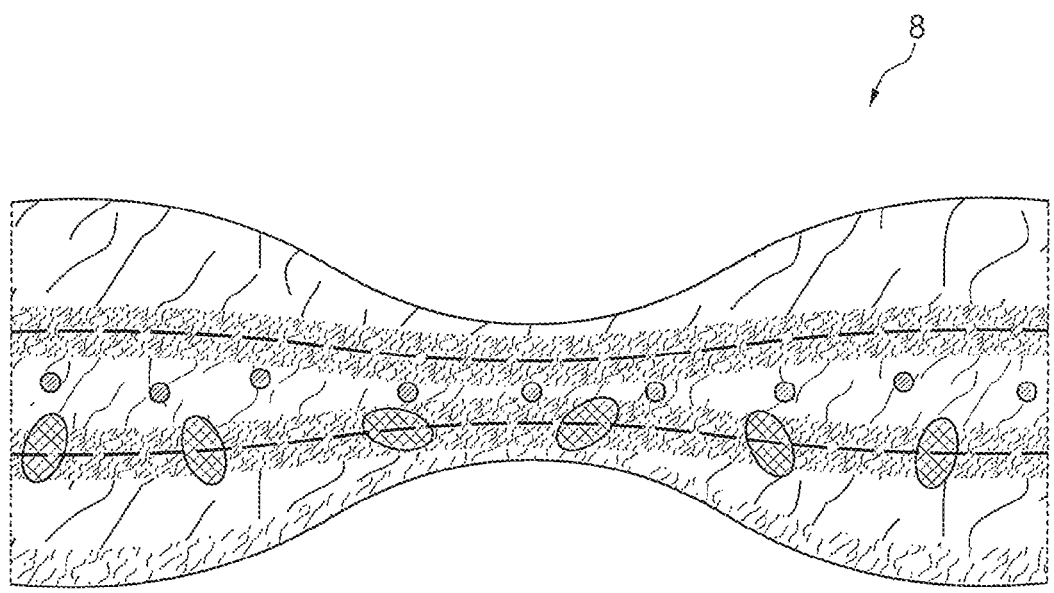

This tendency of standardizing the layers during the deposition- and bonding process is even more visible in FIG. 4 which also includes the material according to FIG. 3. The absorbent structure 8 includes an almost uniform compression of the fibers, in particular through the compression as it has been provided in one bonding portion. The particular air laid layers are not visible any more. Even in portions in which SAP particles are arranged which can be considered as voids during the layer- and interconnection formation no differences are visible with respect to a compression or arrangement of cavities. In the center to lower portion of the absorbent structure, SAP particles are arranged in a random distribution. The material essentially has an even compression. This effect can be generated when layers are used for producing an absorbent structure which essentially include the same material and preferably also a similar material thickness. For example, after the bonding process, the thickness of the layers that are not differentiable from one another anymore is essentially identical respectively. With this prerequisite and due to the fact that the SAP particles are more visible in the lower portion of the absorbent structure, the SAP particles protrude from the liquid storage layer into the liquid distribution layer. This can also be identified through coloration.

Furthermore the option can be derived from FIG. 4 that a mixing zone can be provided. This mixing zone is indicated by a dashed line which is indicated as a center line between two layers, wherein the fibers of one layer mix with the fibers of the other layer in the sections which are emphasized by lines extending perpendicular to the center line.

Figure 5:
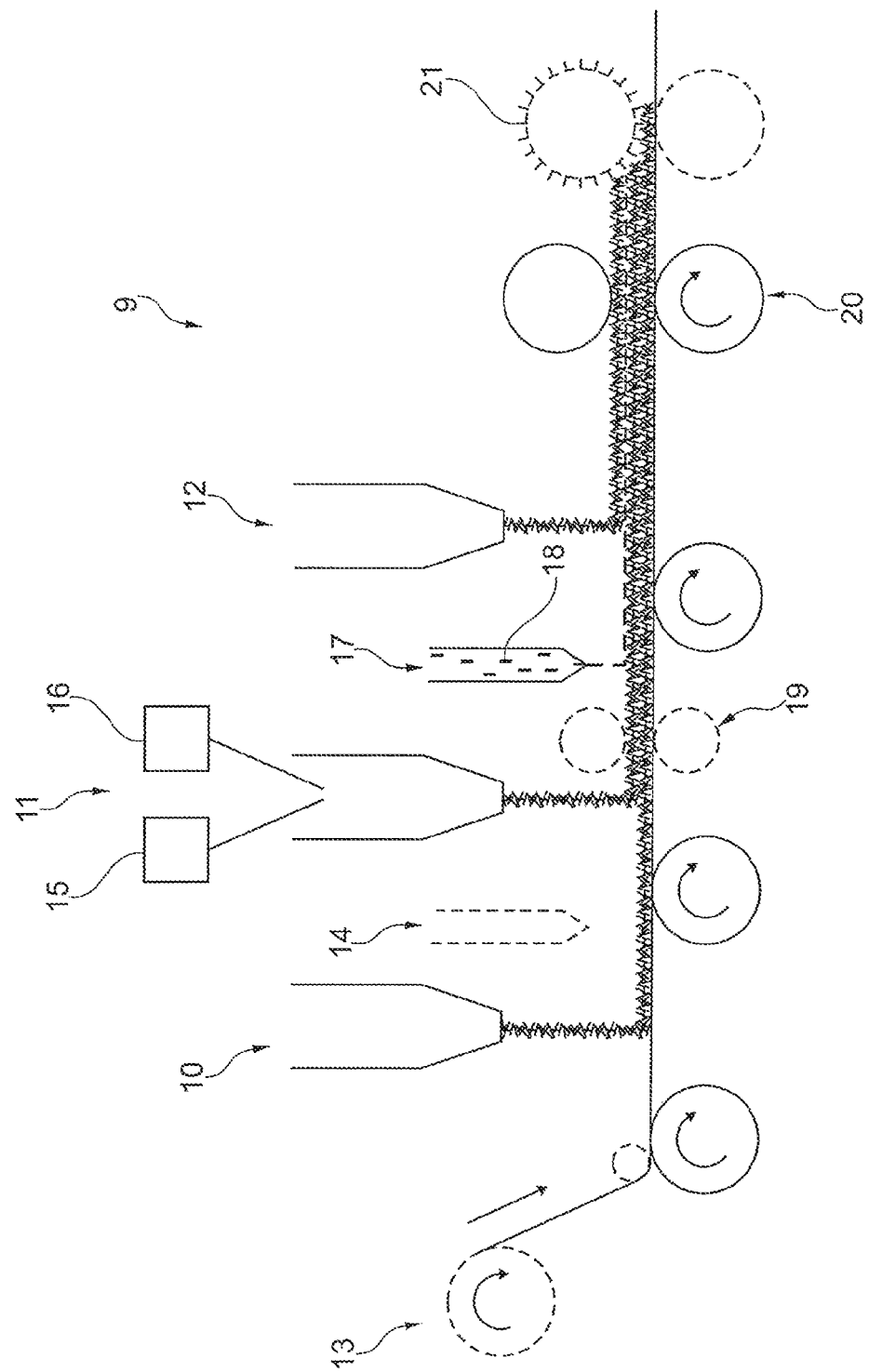
FIG. 5 illustrates a schematic view of a first optional configuration of a production device.

FIG. 5 illustrates a schematic view of an optional configuration of a device 9 for producing an absorbent structure including three air laid layers. The device 9 is illustrated as an in line process with a first, a second and a third air laid forming device 10, 11, 12. It is also illustrated in an exemplary manner that an air laid layer is prefabricated. A roll off calender 13 on the other hand is illustrated in dashed lines. Also two or all air laid layers can be prefabricated and only subsequently joined. Between the first and second air laid forming device 10, 11 for example a first feed 14 can be arranged. The feed 14 is indicated in dashed lines. Through the feed 14 for example SAP material or a bonding material can be fed preferably between two air laid layers. For example, the second air laid forming device 11 mixes a first and a second material 15, 16 with one another before the mix of both materials 15, 16 is also deposited on the perforated band. A mix of this type can for example facilitate mixes of cellulose fibers with bonding fibers, cellulose fibers with SAP fibers and/or particles and also other combinations. A mixture of this type is not only facilitated through the second air laid forming device 11. Rather also the first and/or the third air laid forming device 10, 12 can provide this type of mixture. Between the second and the third air laid forming device 11, 12 a second feed 17 is arranged. Therein, for example, the super absorbent material 18 is supplied which eventually protrudes from the liquid storage layer into the liquid distribution layer. A heating device 19 can, for example, be arranged downstream of the second forming device 11. Here, the heating device 19 is illustrated as a smooth roller calendar. Also, an infra red heater, an oven section or another heater can be provided. Thus, for example, a bonding fiber can be activated so that the fibers of each of both layers respectively bond with one another. By using the smooth roller calender, a pressure can be imparted upon the intermediary material and thus a first compression can be performed. The material supplied through the second feed 18 is then covered by fibers which are deposited by the third air laid forming device 12. Subsequent thereto, a compression can again be performed, for example, through a heated calender 20 configured as compression unit. A compression unit, however, can also provide a compression by hydro jet. A further compression is achieved for example by using a calender with embossings 21. Thus, another surface property can be embossed onto the layer structure, for example, a pattern, a setting of a surface that has remained open, a compression of SAP material from one layer into the next adjacent layer. Furthermore, components can be used in the device and also a basic configuration as evident from WO 00/74620 which is incorporated in its entirety by this reference.

Figure 6:
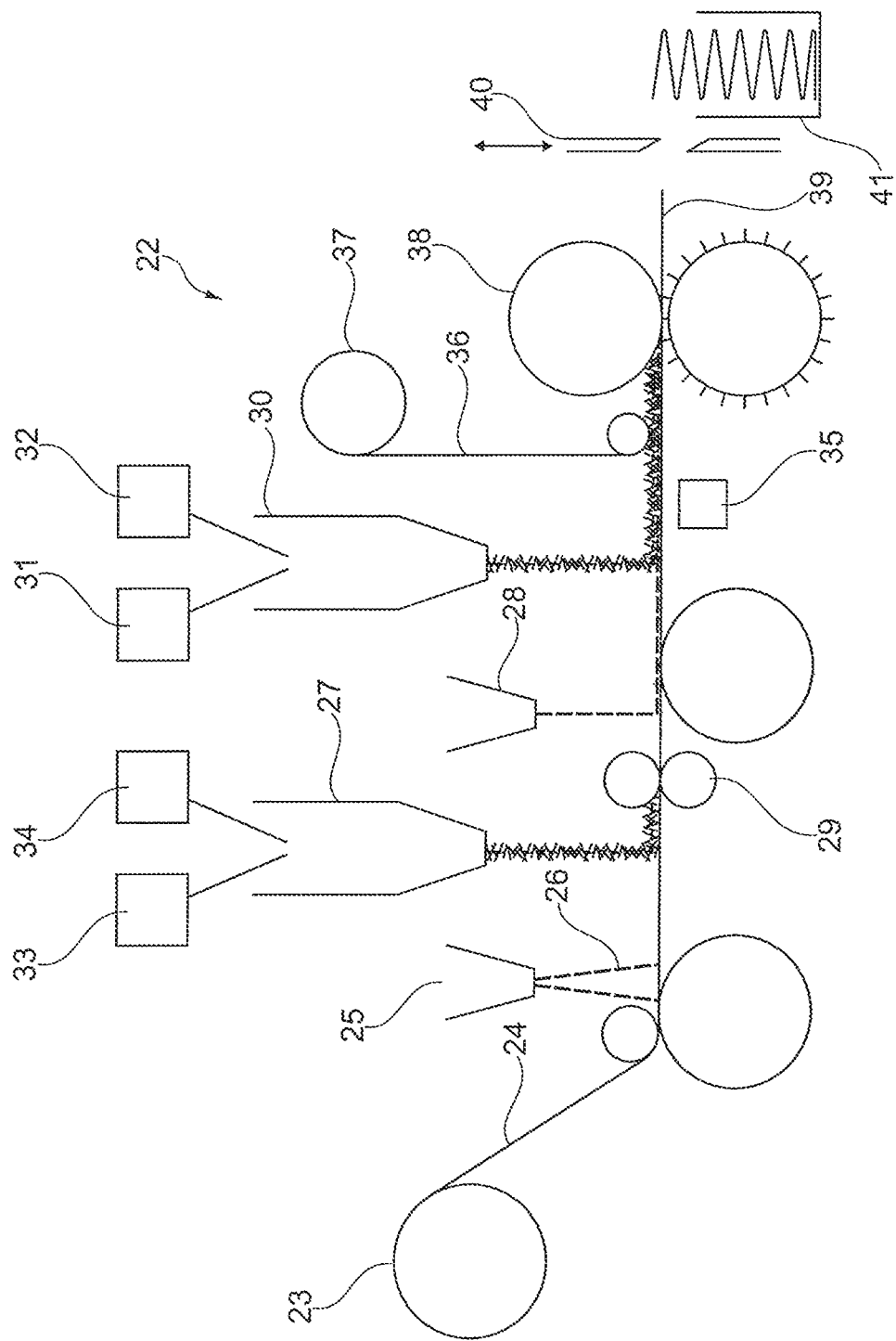
FIG. 6 illustrates a schematic view of a second optional configuration of a production device.

FIG. 6 illustrates a second optional configuration of a manufacturing device 22. From a winder 23, a tissue 24, i.e. a wet laid fiber material, is provided for further processing. The tissue 24 can be provided, for example, through a bonding agent device 25 with a bonding agent 26. The bonding agent 26 can include a bonding fiber, a sprayed on latex application or other means configured for bonding fibers. The bonding agent device 25 does not have to be located at this particular location. The bonding agent device can also be arranged downstream of an air laid depositing device 27 and a SAP supply device 28 for applying first SAP when these have layered their respective materials onto the tissue 24. The bonding agent 26 can also be used to stabilize the position of the SAP, in particular to fixate it. The bonding agent 26 can also be used to change a pore size, in particular make the pore size smaller. Preferably, however, in spite of the bonding agent application, the portion remains air and liquid permeable. The portion can also be partially blocked at least also for liquid. In this illustrated method, the air laid material is deposited on the tissue and compressed and connected through subsequent calendering under heat and pressure. For this purpose, the calender 29 can be heated and variably adjustable with respect to its gap dimension. After the compression of the liquid distribution layer thus formed, an additional air laid material is deposited through a second air laid depositing device 30. The cellulose fibers 31 are thus mixed with the second SAP 32 and jointly deposited thereafter. Before the SAP supply unit can deposit a first SAP 33 directly onto the liquid distribution layer but this is not mandatory. Furthermore also the liquid distribution layer besides cellulose fibers can also include a SAP material 34. In other words, the SAP can be directly mixed with the cellulose fibers and stored in the same supply unit or SAP can be stored in separate supply units and mixed with the cellulose fibers when being laid down by the air laid depositing device 27. The weight portion of first and second SAP together is higher than the total weight portion of the SAP material 34. Through the movement during the production process in particular through a vibrating machine 35 which for example directly impacts the running band causing a migration of SAP into the liquid distribution layer. Thus, the vibration machine 35 can induce the migration with an adjustable frequency that is adapted to the band velocity. A vibration and migration thus induced can also be caused through a movement in the production device itself, for example through a consciously non dampened forwarding of vibrations. Thus, for example, the band movement can be utilized in a controlled manner in order to initiate a migration of the SAP. The tissue 24 preferably has a pore size that is smaller than the SAP size. Therefore, when SAP migrates into the liquid distribution layer or may already be provided there itself, the tissue 24 prevents an exit of the SAP from the perforated band on which the layers are transported. A liquid absorption layer 36 is spooled off from a winder 37 in a prefabricated manner and fed. Preferably, the liquid absorption layer includes thermo plastic fibers. Another calender 38 compresses and connects the layers further with one another through pressure and temperature. An embossing, in particular, an arrangement of heightened bonding portions or protrusions on one of the rollers of the calender is preferably provided on the side oriented towards the liquid distribution layer. An opposite preferred smooth roller, however, is preferably oriented towards the liquid absorption layer 36. Through the calendering, another movement or penetration of SAP from the liquid storage layer into the liquid distribution layer can be provided. Another treatment of the absorbent structure 39 thus formed can be provided directly thereafter, a through cutting unit 40 which preferably separates the particular absorbent structures in longitudinal and transversal direction, wherein the absorbent structures are connected with one another and distributed over the width, or the cutting unit renders the particular absorbent structures transportable, for example through a festooning unit 41. The production device can also provide other materials besides SAP into the mix. Such materials could include odor influencing materials, hydrophilic or hydrophobic embodiments and also colors, indicators, flame inhibitors, foils or similar. Also, a production of absorbent structures can be provided as apparent for example from WO95/03019A1 or WO 03/000163 A1 which are incorporated by this reference in their entirety, but in particular with respect to the strip shape and the cutting.

What is claimed is:

1. A method for producing an absorbent structure, comprising at least the following steps:
    depositing a first layer for configuring a liquid absorption layer which includes at least cellulose;
    depositing a second layer which is air laid for configuring a liquid storage layer which includes at least cellulose fibers and super absorbent polymer chosen from the group consisting of super absorbent polymer particles and super absorbent polymer fibers;
    depositing a third layer which is air laid for forming a liquid distribution layer;
    moving at least one of the first, second and third layers through a heating device in order to bond the same;
    supplying at least one of the first, second and third layers to a calender including at least one smooth roller and an opposite roller which form a calender gap; and
    compressing the at least one of the first, second and third layers within the calender gap, whereby the super absorbent polymer protrudes from the liquid storage layer into the liquid distribution layer and forms a liquid removing contact between the liquid storage layer and the liquid distribution layer, wherein more than 20% of the super absorbent polymer arranged in the liquid storage layer protrudes into the liquid distribution layer.

2. The method according to claim 1, wherein the first layer is an air laid layer which includes cellulose fibers and bi component fibers.

3. The method according to claim 1, wherein the first layer is air laid layer which includes a highly voluminous fleece layer from thermoplastic fibers.

4. The method according to claim 1, further including the step of applying a bonding agent layer on at least one of the first, second and third layers.

5. The method according to claim 4, wherein the bonding agent layer is a latex layer.

6. The method according to claim 1, wherein, in the supplying step, the first, second and third layers are supplied to the calender gap and, in the compressing step, the first, second and third layers are compressed in the calender gap.

7. The method according to claim 1, wherein the opposite roller has protrusions.

* * * * *